United States Patent
Shimizu (10) Patent No.: US 11,863,851 B2
(45) Date of Patent: Jan. 2, 2024

(54) IMAGING UNIT AND ENDOSCOPE

(71) Applicant: OLYMPUS CORPORATION, Tokyo (JP)

(72) Inventor: Toshiyuki Shimizu, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 811 days.

(21) Appl. No.: 16/993,354

(22) Filed: Aug. 14, 2020

(65) Prior Publication Data
US 2020/0367734 A1  Nov. 26, 2020

Related U.S. Application Data

(63) Continuation of application No. PCT/JP2018/034159, filed on Sep. 14, 2018.

(30) Foreign Application Priority Data

Feb. 20, 2018  (JP) .................. 2018-027984

(51) Int. Cl.
*H04N 23/54* (2023.01)
*A61B 1/00* (2006.01)
(Continued)

(52) U.S. Cl.
CPC ......... *H04N 23/54* (2023.01); *A61B 1/00124* (2013.01); *A61B 1/04* (2013.01);
(Continued)

(58) Field of Classification Search
CPC ...... H04N 23/54; H04N 23/50; H04N 23/555; H04N 7/18; A61B 1/00124; A61B 1/04; A61B 1/051; A61B 1/05
(Continued)

(56) References Cited

U.S. PATENT DOCUMENTS 7,074,181 B2 *  7/2006  Futatsugi .................. A61B 1/05
                                                           600/110
2013/0027534 A1   1/2013  Kibayashi
(Continued)

FOREIGN PATENT DOCUMENTS

JP   2005-334509 A   12/2005
JP     4578913 B2   11/2010
(Continued)

OTHER PUBLICATIONS

International Search Report dated Nov. 20, 2018 issued in PCT/JP2018/034159.
(Continued)

*Primary Examiner* — Collin X Beatty
(74) *Attorney, Agent, or Firm* — Scully, Scott, Murphy & Presser, P.C.

(57) ABSTRACT

An imaging unit includes: a semiconductor package including an imaging device and having a back surface on which a sensor electrode is formed; a circuit substrate including a connection electrode that is connected to the sensor electrode via a bump; a surrounding part configured to cover the semiconductor package and the circuit substrate; a filler with which a space that is enclosed by the surrounding part is filled to seal a circumference of the semiconductor package and the circuit substrate; and a first cover configured to prevent the filler from infiltrating a joint between the semiconductor package and the circuit substrate.

6 Claims, 10 Drawing Sheets

(51) Int. Cl.
  *A61B 1/05* (2006.01)
  *A61B 1/04* (2006.01)
  *H04N 23/50* (2023.01)

(52) U.S. Cl.
  CPC ............ *A61B 1/051* (2013.01); *H04N 23/50* (2023.01); *H04N 23/555* (2023.01)

(58) Field of Classification Search
  USPC .......................................................... 359/689
  See application file for complete search history.

(56) References Cited

U.S. PATENT DOCUMENTS

| | | | |
|---|---|---|---|
| 2013/0329026 A1 | 12/2013 | Hida et al. | |
| 2014/0185140 A1* | 7/2014 | Kawai | G02B 27/0006 359/508 |
| 2015/0312457 A1* | 10/2015 | Kojima | G02B 23/2484 29/840 |
| 2016/0205296 A1* | 7/2016 | Igarashi | A61B 1/0008 348/76 |
| 2019/0021582 A1* | 1/2019 | Shimizu | A61B 1/044 |

FOREIGN PATENT DOCUMENTS

| | | | |
|---|---|---|---|
| JP | 2013-175861 A | 9/2013 | |
| JP | 2014-133046 A | 7/2014 | |
| JP | 6293391 B1 | 3/2018 | |
| WO | WO 2012/137739 A1 | 10/2012 | |
| WO | WO-2013019795 A1 * | 2/2013 | ............... B60R 1/00 |
| WO | WO 2013/146091 A1 | 10/2013 | |
| WO | WO 2017/199776 A1 | 11/2017 | |
| WO | WO-2018155066 A1 * | 8/2018 | ......... A61B 1/00009 |

OTHER PUBLICATIONS

English Abstract of corresponding JP 2006094955 A, dated Apr. 13, 2006.

\* cited by examiner

IMAGING UNIT AND ENDOSCOPE

CROSS-REFERENCE TO RELATED APPLICATION

This application is a continuation of PCT International Application No. PCT/JP2018/034159 filed on Sep. 14, 2018, which designates the United States, incorporated herein by reference, and which claims the benefit of priority from Japanese Patent Application No. 2018-027984, filed on Feb. 20, 2018, incorporated herein by reference.

BACKGROUND

1. Technical Field

The present disclosure relates to an imaging unit that is arranged in a distal end of an insertion unit of an endoscope configured to be inserted into a subject and that captures in-vivo images of the subject and to an endoscope.

2. Related Art

In the field of medicine and the field of industry, endoscopic devices have been widely used for various examinations. Among them, medical endoscopic devices are widely used because they make it possible to acquire in-vivo images of a body cavity of a subject, such as a patent, without incising the subject by inserting an elongated and flexible insertion unit having a distal end on which an imaging device is arranged into the body cavity and furthermore to perform treatment processing by causing a treatment tool to protrude from the distal end of the insertion unit as required.

Into such a distal end of an insertion unit of an endoscopic device, an imaging unit including an imaging device, a circuit substrate on which electronic parts, such as a capacitor and an IC chip, and cables that form a drive circuit of the imaging device, electric connection parts, such as TAB tapes, that connect the imaging device and the circuit substrate is fitted and the area around the imaging device and the electronic parts is filled with a filler for the purpose of protection.

Autoclave sterilization (115° C. to 138° C. and an atmospheric pressure of approximately +0.2 MPa) is performed on endoscopes used for medicine for disinfection and sterilization and, when the temperature is increased to a sterilization temperature, there is a risk that the joint between the TAB tapes and the electronic parts may be broken due to expansion of the filler and therefore an imaging unit in which two types of sealing resin with different linear expansion coefficients has been proposed (For example, refer to Japanese Patent No. 4578913).

Furthermore, an imaging unit for which a chip size package (CSP) in which the size of an imaging device chip directly corresponds to the size of the semiconductor package is used and in which sensor electrodes of the CSP and connection electrodes of a circuit substrate are directly connected to each other with bumps, or the like, has been proposed. In the imaging unit, a second filler whose linear expansion per unit length at a sterilization temperature is smaller than that of a first filler with which the inside of a surrounding part covering the semiconductor package is filled is applied to the surface of the joint between the semiconductor package and the circuit substrate, thereby increasing reliability of the joint (For example, Japanese Patent No. 6293391).

SUMMARY

In some embodiments, an imaging unit includes: a semiconductor package including an imaging device and having a back surface on which a sensor electrode is formed; a circuit substrate including a connection electrode that is connected to the sensor electrode via a bump; a surrounding part configured to cover the semiconductor package and the circuit substrate; a filler with which a space that is enclosed by the surrounding part is filled to seal a circumference of the semiconductor package and the circuit substrate; and a first cover configured to prevent the filler from infiltrating a joint between the semiconductor package and the circuit substrate.

In some embodiments, an endoscope includes an insertion unit having a distal end in which the imaging unit is arranged.

The above and other features, advantages and technical and industrial significance of this disclosure will be better understood by reading the following detailed description of presently preferred embodiments of the disclosure, when considered in connection with the accompanying drawings.

DETAILED DESCRIPTION

In the following description, an endoscope system including an imaging unit will be described as modes for carrying out the disclosure ("embodiment" below). The embodiments do not limit the disclosure. In the description of the drawings, the same components are denoted by the same reference numbers. Not that the drawings are schematic and the relation between the thickness and width of each member, the ratio of each member, etc., are different from actual ones. The drawings contain parts whose sizes and ratios differ among the drawings.

First Embodiment

Figure 1:
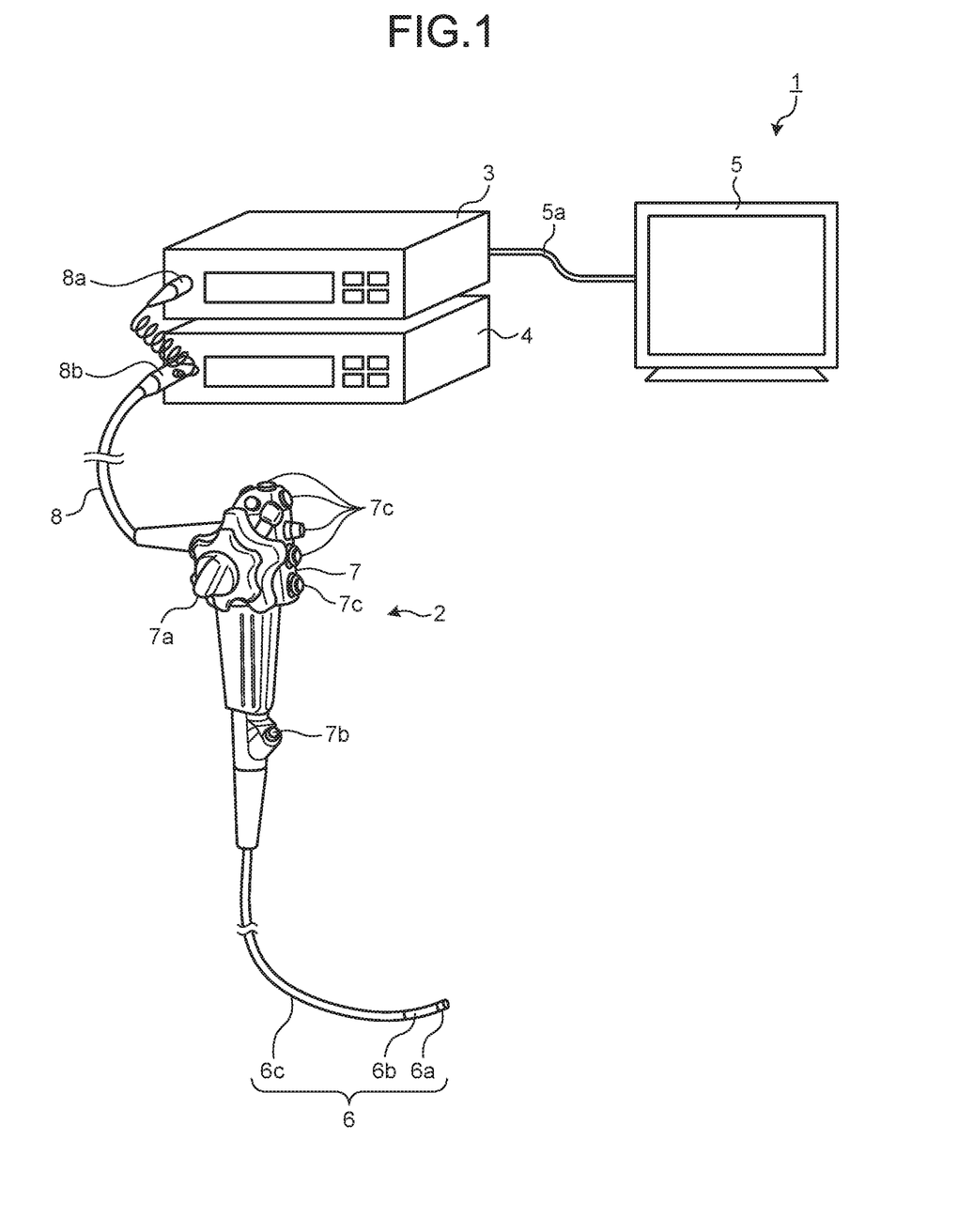
FIG. 1 is a diagram schematically illustrating an entire configuration of an endoscope system according to a first embodiment of the disclosure.

FIG. 1 is a diagram schematically illustrating an overall configuration of an endoscope system according to a first embodiment of the disclosure. As illustrated in FIG. 1, an endoscope system 1 according to the first embodiment includes an endoscope 2 that is inserted into a subject, captures an in-vivo image of the subject, and generates an in-vivo image signal of the subject; an information processing device 3 that performs given image processing on the signal of the image captured by the endoscope 2 and controls each unit of the endoscope system 1; a light source device 4 that generates illumination light of the endoscope 2; and a display device 5 that displays an image of the image signal on which the image processing has been performed by the information processing device 3.

The endoscope 2 includes an insertion unit 6 that is inserted into the subject, an operation unit 7 that is arranged on the side of a proximal end part of the insertion unit 6 and that is held by a practitioner, and a flexible universal cord 8 that extends from the operation unit 7.

The insertion unit 6 is implemented using an illumination fiber (light guide cable), an electronic cable, an optical fiber, etc. The insertion unit 6 includes a distal end part 6a incorporating an imaging unit to be described below, a curve part 6b that flexibly curves and that is formed of multiple curve members, and a flexible tube 6c that is flexible and that is arranged on the side of a proximal end part of the curve part 6b. In the distal end part 6a, an illuminator that illuminates the inside of the subject via an illumination lens, an observation unit that captures an in-vivo image of the subject, an opening that communicates a treatment tool channel, and an air transmission and water transmission nozzle (not illustrated in the drawings) are arranged.

The operation unit 7 includes a curve knob 7a that causes the curve part 6b to curve vertically and horizontally, a treatment tool insertion unit 7b through which a treatment tool, such as a biological forceps or a laser scalpel, is inserted into a body cavity of the subject, and a plurality of switch parts 7c for operating peripherals, such as the information processing device 3, the light source device 4, an air transmission device, a water transmission device, and a gas transmission device. The treatment tool that is inserted from the treatment tool insertion unit 7b comes out of the opening at the distal end of the insertion unit 6 via the treatment tool channel that is formed inside.

The universal cord 8 is configured using an illumination fiber, a cable, etc. The universal cord 8 bifurcates at the proximal end and the end of one of the branches is a connector 8a and the proximal end of the other branch is a connector 8b. The connector 8a is detachable from the connector of the information processing device 3. The connector 8b is detachable from the light source device 4. The universal cord 8 transmits illumination light that is emitted from the light source device 4 to the distal end part 6a via the connector 8b and the illumination fiber. The universal cord 8 transmits the signal of the image that is captured by the imaging unit to be described below to the information processing device 3 via the cable and the connector 8a.

The information processing device 3 performs the given image processing on the image signal that is output from the connector 8a and controls the entire endoscope system 1.

The light source device 4 is configured using a light source that emits light, a condenser lens, etc. Under the control of the information processing device 3, the light source device 4 emits light from the light source and supplies the light as the illumination light to the inside of the subject that is a subject to the endoscope 2 to which the light source device 4 is connected via the connector 8b and the illumination fiber of the universal cord 8.

The display device 5 is configured using a display using liquid crystals or organic electro luminescence (EL). The display device 5 displays various types of information containing the image on which the given image processing has been performed by the information processing device 3 via a video cable 5a. This allows the practitioner to operate the endoscope 2 while looking at the image (in-vivo image) that is displayed by the display device 5 and accordingly observe a desired position in the subject and determine characterization.

Figure 2:
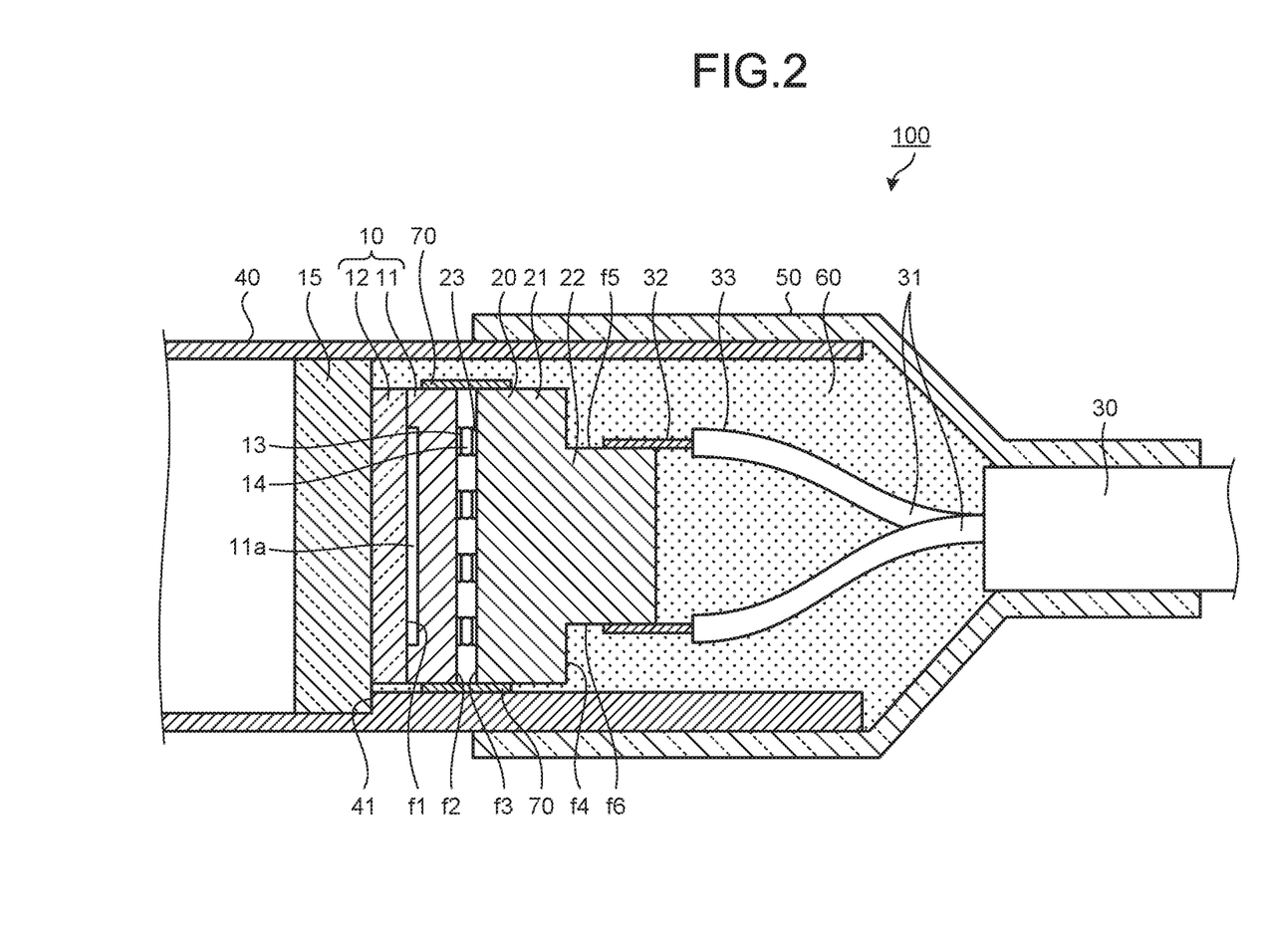
FIG. 2 is a cross-sectional view of an imaging unit that is arranged in a distal end part of an endoscope illustrated in FIG. 1.
Figure 3:
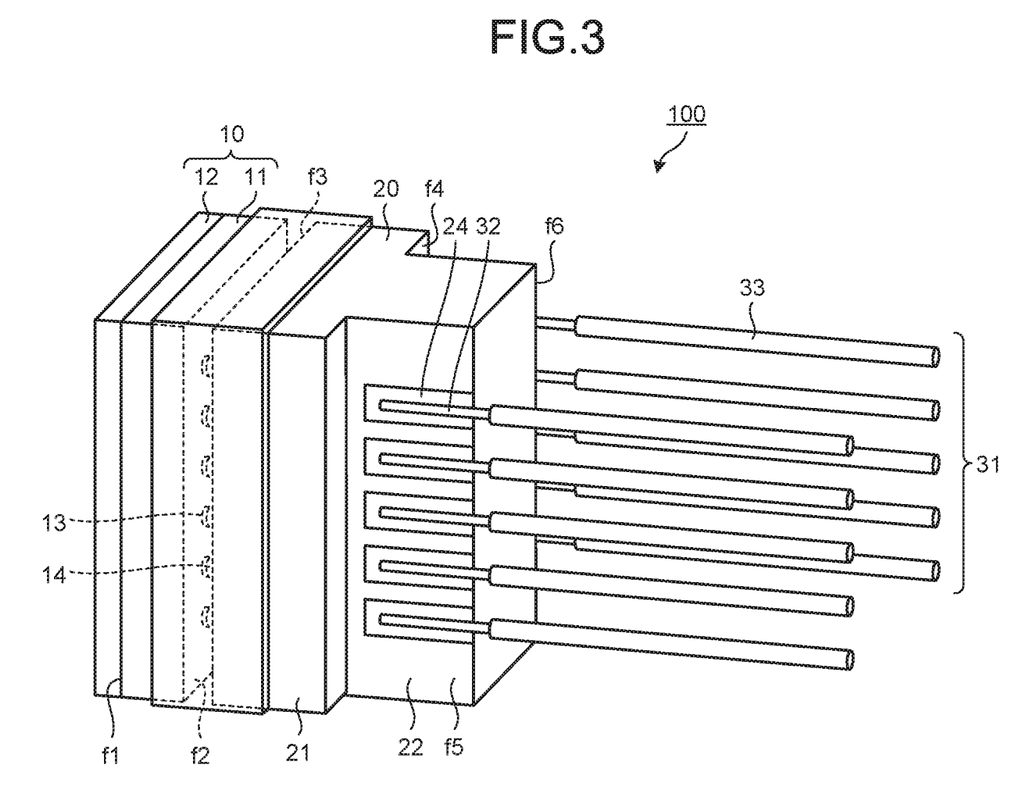
FIG. 3 is a perspective view of the imaging unit illustrated in FIG. 2.

The imaging unit that is used in the endoscope system 1 will be described in detail. FIG. 2 is a cross-sectional view of an imaging unit 100 that is arranged at the distal end part of the endoscope illustrated in FIG. 1. FIG. 3 is a perspective view of the imaging unit 100 illustrated in FIG. 2. FIG. 3 does not illustrate a holder frame 40, a heat shrinkable tube 50, a filler 60, and a centering cover glass 15 and illustrates the imaging unit 100 rotated by 90 degrees with a side surface f5 of a circuit substrate 20 being on the front side.

The imaging unit 100 includes a semiconductor package 10 including an imaging device 11 that converts an optical image that is formed by an optical system on a front surface f1 into an image signal and that has a back surface f2 on which sensor electrodes 13 are formed; the circuit substrate 20 including a body 21 on which connection electrodes 23 are formed and an attachment part 22 that protrudes from a back surface of the body 21; an assembly cable 30 including a plurality of signal cables 31 that are twisted together; the holder frame 40 that holds the semiconductor package 10; the heat shrinkable tube 50 that covers the proximal end part of the holder frame 40; the filler 60 with which the space enclosed, that is, surrounded by the holder frame 40 and the heat shrinkable tube 50 is filled; and a cover member 70 that coats a side surface of the semiconductor package 10 and a side surface of the circuit substrate 20 together. In the first embodiment, the holder frame 40 and the heat shrinkable tube 50 function as a surrounding part and the holder frame 40 and the heat shrinkable tube 50 surround the semiconductor package 10 and the circuit substrate 20.

The semiconductor package 10 is attached such that a cover glass 12 protects a light receiver 11a of the imaging device 11 and the centering cover glass 15 having a diameter larger than that of the semiconductor package 10 is attached to the side of a distal end of the cover glass 12. An outer circumferential part of the centering cover glass 15 not contacting the semiconductor package 10 abuts on a positioning part 41 of the holder frame 40, thereby being held by the holder frame 40. Light that is converged by a lens unit is incident on a light receiving surface of the imaging device 11 via the centering cover glass 15 and the cover glass 12. The sensor electrodes 13 and bumps 14 formed of solder, or the like, are formed on a surface f2 of the imaging device 11. It is preferable that the semiconductor package 10 be a chip size package (CSP) that is obtained by performing interconnecting, electrode formation, resin sealing, and dicing on imaging device chips on a wafer and in which the size of the imaging device chip directly serves as the size of the semiconductor package eventually.

The circuit substrate 20 includes the body 21 and the attachment part 22. The connection electrodes 23 is formed on a front surface f3 of the body 21. The attachment part 22 protrudes from a back surface f4 of the body 21. Cable connection electrodes 24 are formed on two side surfaces f5 and f6 that are opposed to each other among protruding side walls of the attachment part 22. The body 21 and the attachment part 22 may be integrally formed into a substrate or a combination of substrates that are prepared individually.

The circuit substrate 20 includes a plurality of substrates on which interconnects are formed and that are laminated, thereby forming a platy shape (substrates parallel with the front surface f3 and the back surface f4 are laminated). Ceramics substrates, glass epoxy substrates, flexible substrates, glass substrates, silicon substrates, or the like, are used as the laminated substrates. In the circuit substrate 20, a plurality of vias (not illustrated in the drawings) that make the interconnects on the laminated substrates conduct are formed.

On the front surface f3 of the body 21 of the circuit substrate 20, the connection electrodes 23 are formed and the connection electrodes 23 are electrically and mechanically connected to the sensor electrodes 13 of the semiconductor package 10 via the bumps 14.

The assembly cable 30 is formed of signal cables 31 that are 10 single cables and the outer circumference of the signal cables 31 is covered with an integrated shield and an integrated coating. The integrated shield and the integrated coating are removed from the distal end part of the assembly cable 30. The signal cable 31 includes a core 32 and a shield 33 that is formed on the outer circumference of the core 32. The shield 33 is removed from the distal end part of the signal cable 31 such that the core 32 is exposed gradually from the distal end part. In the first embodiment, the core 32 of the signal cable 31 is electrically and mechanically connected to the cable connection electrode 24 that is formed on the opposed side surfaces f5 and f6 of the attachment part 22 of the circuit substrate 20 via a solder not illustrated in the drawings, or the like. In the first embodiment, the circuit substrate 20 and the signal cables 31 (the assembly cable 30) that are connected respectively to the cable connection electrodes 24 on the side surface f5 and the side surface f6 of the circuit substrate 20 have sizes that fall within a projection plane of the semiconductor package 10 in an optical-axis direction. This makes it possible to thin the imaging unit 100.

The heat shrinkable tube 50 covers the side of the distal end of the assembly cable 30 from the proximal end part of the holder frame 40 and is adhered to and fixed to the holder frame 40 and the integrated coating of the assembly cable 30. The space enclosed by the holder frame 40 and the heat shrinkable tube 50 is filled with the filler 60 that is insulative. The filler 60 is made of a material that is highly damp proofing and thus makes it possible to reduce the effects of humidity on the semiconductor package 10 and the circuit substrate 20.

The circumference of the joint between the semiconductor package 10 and the circuit substrate 20, that is, part of the side surface of the semiconductor package 10 and part of the side surface of the body 21 of the circuit substrate 20 are covered with the cover member 70 that prevents the filler 60 from infiltrating the joint. Covering the circumference of the joint between the semiconductor package 10 and the circuit substrate 20 with the cover member 70 forms an internal space around the joints each between the sensor electrode 13 and the connection electrode 23 and the air is present in the internal space. The elastic modulus of air is significantly smaller than that of a general filler and thus the air has small effects on the joints when the temperature is increased to the sterilization temperature, which makes it possible to keep reliability of the joints even in the sterilization processing for a long period. In addition to adhering an adhesive resin film to the circumference of the joint between the semiconductor package 10 and the circuit substrate 20 and covering the circumference of the joint between the semiconductor package 10 and the circuit substrate 20 with the heat shrinkable tube, sealing the circumference of the joint with a O-ring or square ring made of rubber serves as the cover member 70 and makes it possible to prevent the filler 60 from infiltrating the joint.

In the imaging unit 100 according to the first embodiment, covering the side surface of the semiconductor package 10 and the side surface of the circuit substrate 20 with the cover member 70 forms the internal space in which air is present around the joints, which makes it possible to reduce the effects on the joints during the sterilization processing. Even when a material with large linear expansion is used as the filler 60, it is possible to reduce the effects of humidity on the semiconductor package 10 and the circuit substrate 20 and reduce the effects on the joints during the sterilization processing. The circuit substrate 20 and the signal cables 31 (the assembly cable 30) that are connected respectively to the cable connection electrodes 24 on the side surface f5 and the side surface f6 of the circuit substrate 20 have sizes that fall within the projection plane of the semiconductor package 10 in the optical-axis direction, which makes it possible to thin the imaging unit 100.

Second Embodiment

Figure 4:
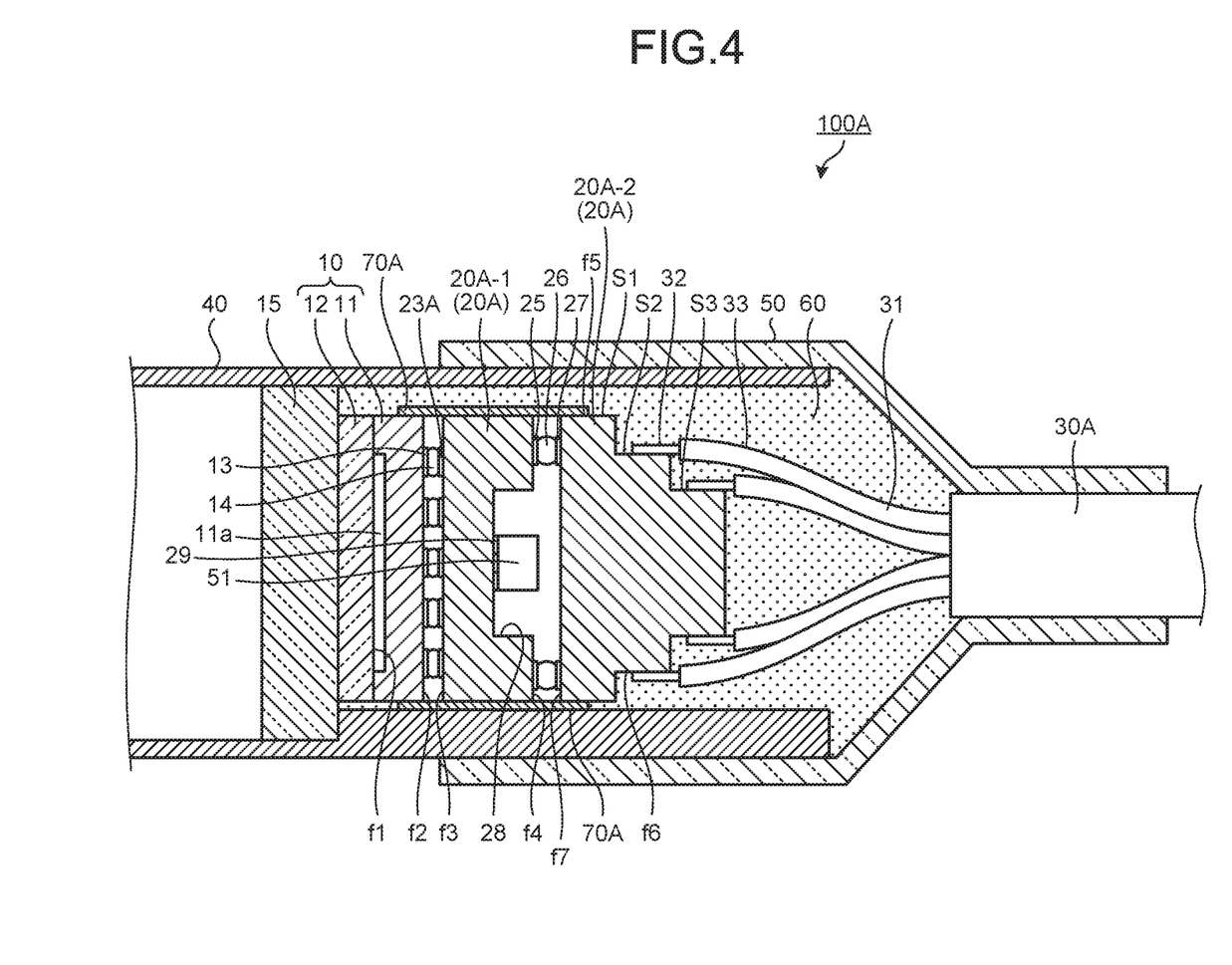
FIG. 4 is a cross-sectional view of an imaging unit according to a second embodiment of the disclosure.
Figure 5:
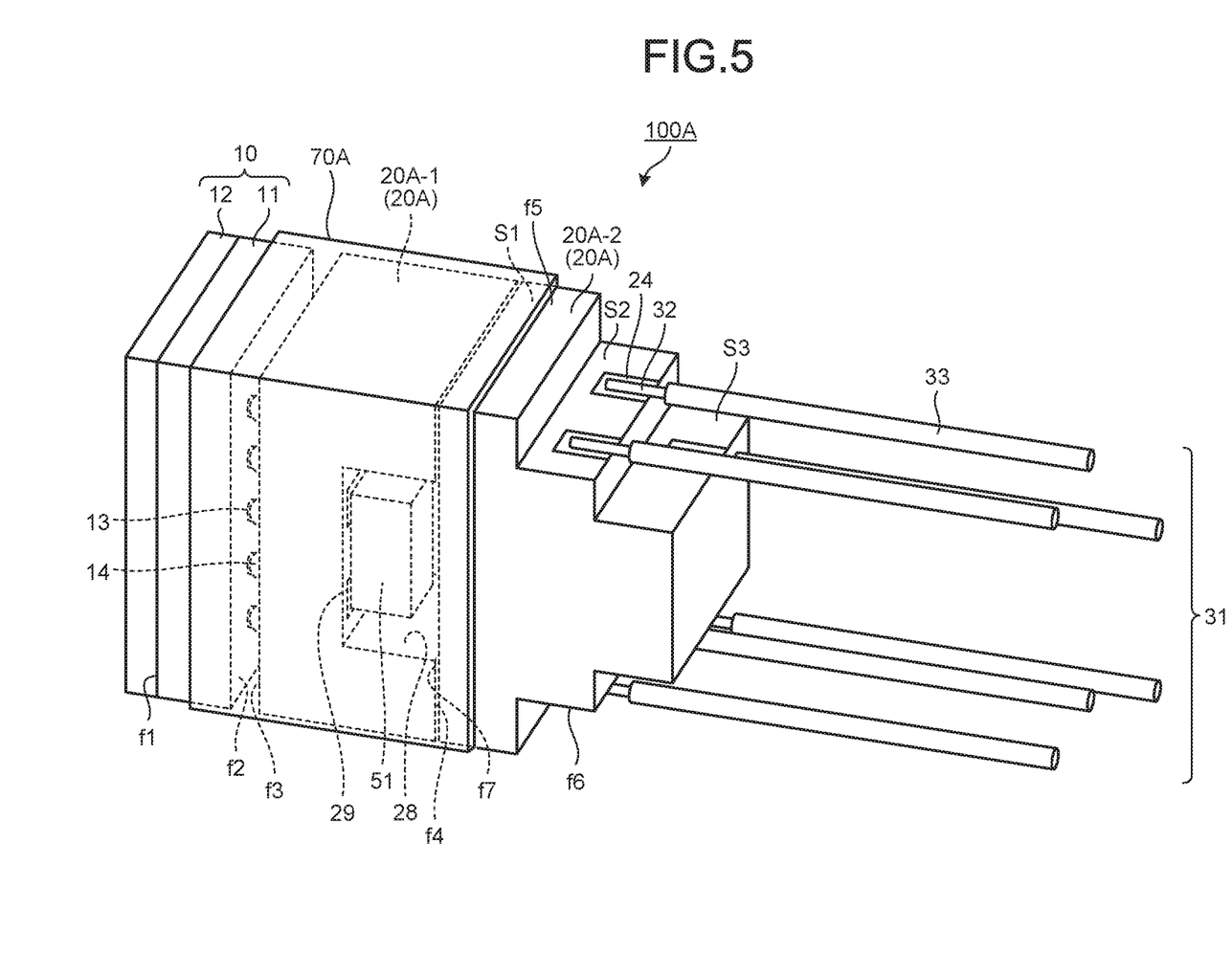
FIG. 5 is a perspective view of the imaging unit illustrated in FIG. 4.

FIG. 4 is a cross-sectional view of an imaging unit 100A according to a second embodiment of the disclosure. FIG. 5 is a perspective view of the imaging unit 100A illustrated in FIG. 4. Illustration of the holder frame 40, the heat shrinkable tube 50, the filler 60, and the centering cover glass 15 is omitted from FIG. 5.

In the imaging unit 100A according to the second embodiment, a circuit substrate 20A includes a first circuit substrate 20A-1 and a second circuit substrate 20A-2. On the first circuit substrate 20A-1, first connection electrodes 23A and second connection electrodes 25 are formed respectively on the front surface f3 and the back surface f4 and the first connection electrodes 23A on the side of the front surface f3 are electrically and mechanically connected to the sensor electrodes 13 of the semiconductor package 10 via the bumps 14. In the second circuit substrate 20A-2, third connection electrodes 27 are formed on a front surface f7, cable connection electrodes 24 are formed on a side surface f5 and a side surface f6 that are opposed to each other and that are stepped such that the side surfaces f5 and f6 get close to each other on the proximal end side, and the third connection electrodes 27 are electrically and mechanically connected to the second connection electrodes 25 of the first circuit substrate 20A-1 via bumps 26. Solder balls, metal core solder ball, resin core balls, or gold bumps serve as the bumps.

A concave 28 is formed on the back surface of the first circuit substrate 20A-1 and an electronic part 51 is mounted on a mount land 29 that is formed in the concave 28 via a conductive member, such as solder. It is preferable that the first circuit substrate 20A-1 be formed of a material with high thermal conductivity from the standpoint of efficient heat dissipation of heat that is generated by the imaging device 11. For example, alumina, aluminum nitride, beryllia, or silicon carbide is exemplified.

The second circuit substrate 20A-2 has steps S1, S2, and S3 on the side surface f5 and the side surface f6 that are side surfaces opposed to each other. The steps S1 to S3 are formed such that the side surface f5 and the side surface f6 get close to each other on the proximal end side in the optical-axis direction of the semiconductor package 10. The cable connection electrodes 24 are arranged on the steps S2 and S3 and the cores 32 of the signal cables 31 are electrically and mechanically connected to the cable connection electrodes 24. It is preferable that the second circuit substrate 20A-2 be formed of a material with low thermal conductivity from the standpoint of reducing heat dissipation in the second circuit substrate 20A-2 for easy soldering. For example, a low temperature Co-fired ceramics (LTCC) substrate in which glass components are mixed into aluminum nitride is exemplified. In addition to the standpoint of soldering, silver or copper with small resistance is usable as electrodes in the LTCC substrate and is referable because the signal transmission rate can be increased.

In the imaging unit 100A, the first circuit substrate 20A-1, the second circuit substrate 20A-2, and the signal cables 31 (an assembly cable 30A) that are connected respectively to the cable connection electrodes 24 have sizes that fall within the projection plane of the semiconductor package 10 in the optical axis direction, which makes it possible to thin the imaging unit 100A.

The circumference of the joint between the semiconductor package 10 and the first circuit substrate 20A-1 and the circumference of the joint between the first circuit substrate 20A-1 and the second circuit substrate 20A-2, that is, part of the side surface of the semiconductor package 10, the whole side surface of the first circuit substrate 20A-1, and part of the side surface of the second circuit substrate 20A-2 are covered with a cover member 70A that prevents the filler 60 from infiltrating the joints. Covering the joint between the semiconductor package 10 and the first circuit substrate 20A-1 and the joint between the first circuit substrate 20A-1 and the second circuit substrate 20A-2 with the cover member 70A forms an internal space in which air is present around the joints each between the sensor electrode 13 and the first connection electrode 23A, the joints each between the second connection electrode 25 and the third connection electrode 27, and the joints each between the electronic part 51 and the mount land 29. In the second embodiment, the single cover member 70A covers the circumference of the joint between the semiconductor package 10 and the first circuit substrate 20A-1 and the circumference of the joint between the first circuit substrate 20A-1 and the second circuit substrate 20A-2. Alternatively, the circumference of the joint between the semiconductor package 10 and the first circuit substrate 20A-1 and the circumference of the joint between the first circuit substrate 20A-1 and the second circuit substrate 20A-2 may be covered with individual covers, respectively, if the concave 28 is sealed.

In the imaging unit 100A according to the second embodiment, covering part of the side surface of the semiconductor package 10, the whole side surface of the first circuit substrate 20A-1, and part of the side surface of the second circuit substrate 20A-2 with the cover member 70A forms the internal space in which air is present around the joint, which makes it possible to reduce the effect on the joint during sterilization processing. Even when a material with large liner expansion is used as the filler 60, it is possible to reduce the effect of humidity on the semiconductor package 10, the first circuit substrate 20A-1, and the second circuit substrate 20A-2 and reduce the effect on the joints during sterilization processing. The first circuit substrate 20A-1, the second circuit substrate 20A-2, and the signal cables 31 (the assembly cable 30) that are connected respectively to the cable connection electrodes 24 on the sides surface f5 and the side surface f6 of the second circuit substrate 20A-2 have sizes that fall within the projection plane of the semiconductor package 10 in the optical-axis direction, which makes it possible to thin the imaging unit 100A.

Figure 6:
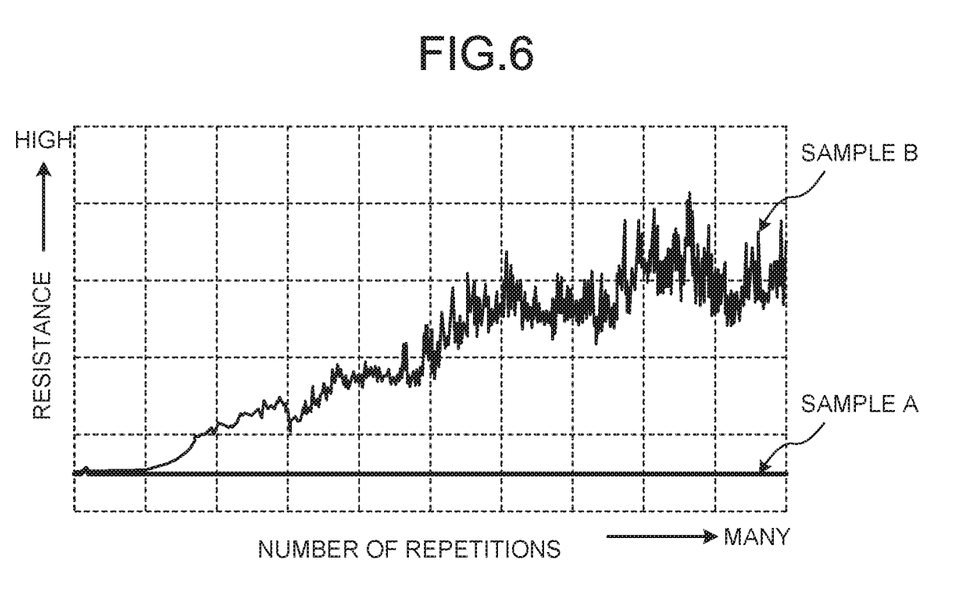
FIG. 6 is a diagram illustrating transition of resistance in durability tests.

The effect of preventing the filler from infiltrating the circumferences of the joints and forming the internal space where air is present around the joints are obvious from FIG. 6. FIG. 6 is a diagram illustrating transition of resistance in a durable test. FIG. 6 is a diagram illustrating transition of resistance in the joints (the joints each between the sensor electrode 13 and the first connection electrode 23A, the joints each between the second connection electrode 25 and the third connection electrode 27, and the joints each between the electronic part 51 and the mount land 29) at a high temperature that is obtained by performing durable tests in which a sample A in which air is present around the joint between the semiconductor package 10 and the first circuit substrate 20A-1 and the joint between the first circuit substrate 20A-1 and the second circuit substrate 20A-2 and a sample B that serves as a comparison and in which a filler is ejected around the joint between the semiconductor package 10 and the first circuit substrate 20A-1 and the joint between the first circuit substrate 20A-1 and the second circuit substrate 20A-2. As illustrated in FIG. 6, it could be confirmed that no increase in resistance is shown in the sample A in which air is present around the joint even when the number of repletion of durable tests increases. On the other hand, an increase in renitence according to an increase in the number of durable tests is shown in the sample B that is filled with the filler 60.

In the second embodiment, covering the circumference of the joint between the semiconductor package 10 and the first circuit substrate 20A-1 and the circumference of the joint between the first circuit substrate 20A-1 and the second circuit substrate 20A-2 with the cover member 70A prevents the filler 60 from infiltrating the joints. Alternatively, without using the independent cover member 70A, it is possible to prevent the filler 60 from infiltrating the joints with a heat shrinkable tube.

Figure 7:
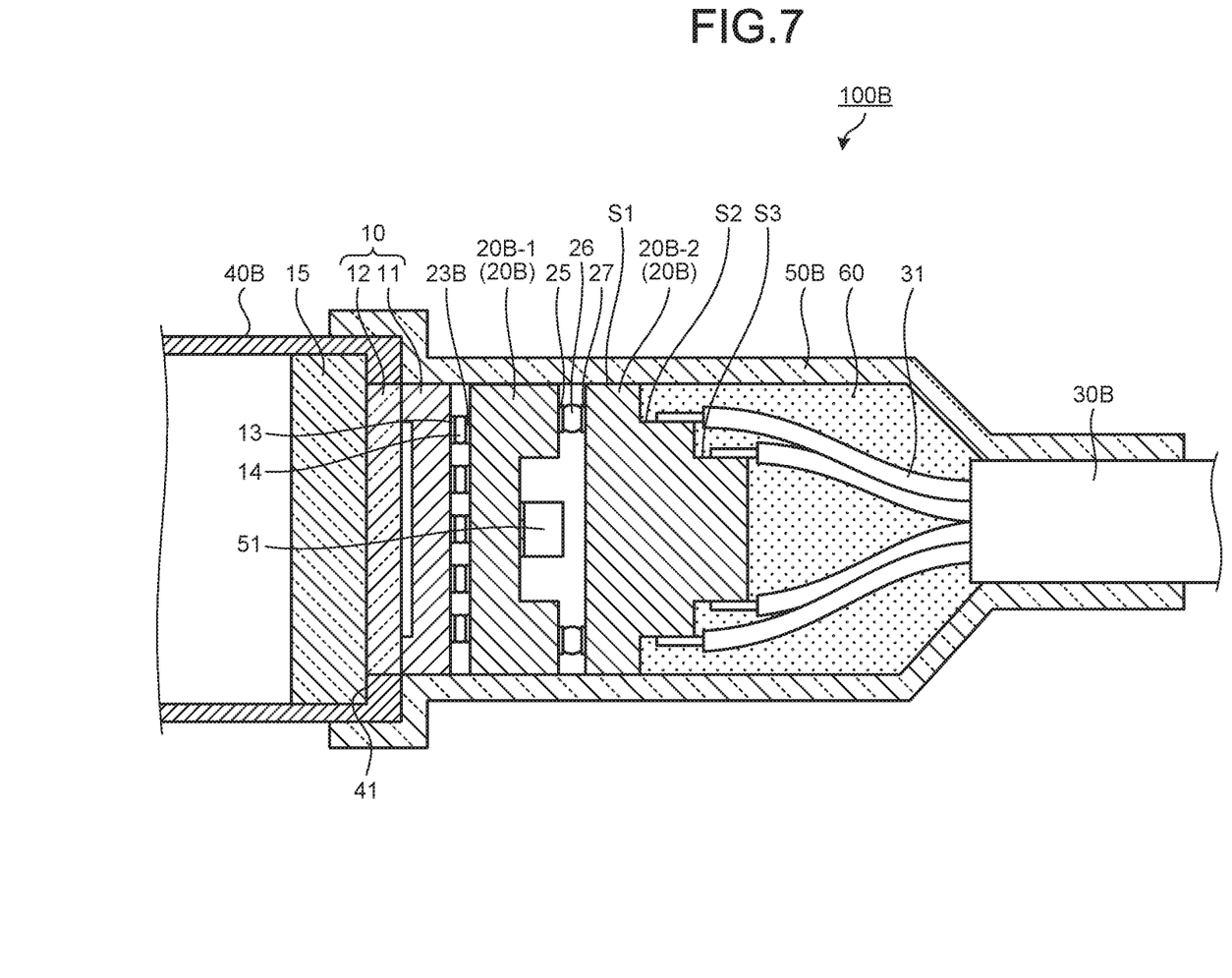
FIG. 7 is a cross-sectional view of an imaging unit according to a modification of the second embodiment of the disclosure.

FIG. 7 is a cross-sectional view of an imaging unit 100B according to a modification of the second embodiment of the disclosure. In the imaging unit 100B, a holder frame 40B is present on the proximal end side only up to the length of the positioning part 41 on which the centering cover glass 15 abuts and a heat shrinkable tube 50B covers the side surface of the holder frame B on the proximal end side, the side surface of the semiconductor package 10, a side surface of a first circuit substrate 20B-1, and a side surface (only the step S1) of a second circuit substrate 20B-2.

In the imaging unit 100B according to the modification of the second embodiment, covering the side surface of the semiconductor package 10, the side surface of the first circuit substrate 20B-1, and the side surface (the step S1) of the second circuit substrate 20B-2 with the heat shrinkable tube 50B forms the internal space in which air is present around the joints, which reduces the effect on the joints during sterilization processing. As in the second embodiment, using a material with a great damp proofing property as the filler 60 enables reduction of effects of moisture on the semiconductor package 10, the first circuit substrate 20B-1, and the second circuit substrate 20B-2. The first circuit substrate 20B-1, the second circuit substrate 20B-2, and the signal cables 31 (the assembly cable 30) that are connected respectively to the cable connection electrodes 24 on the sides surface f5 and the side surface f6 of the second circuit substrate 20B-2 have sizes that fall within the projection plane of the semiconductor package 10 in the optical-axis direction, which makes it possible to thin the imaging unit 100B.

Third Embodiment

Figure 8:
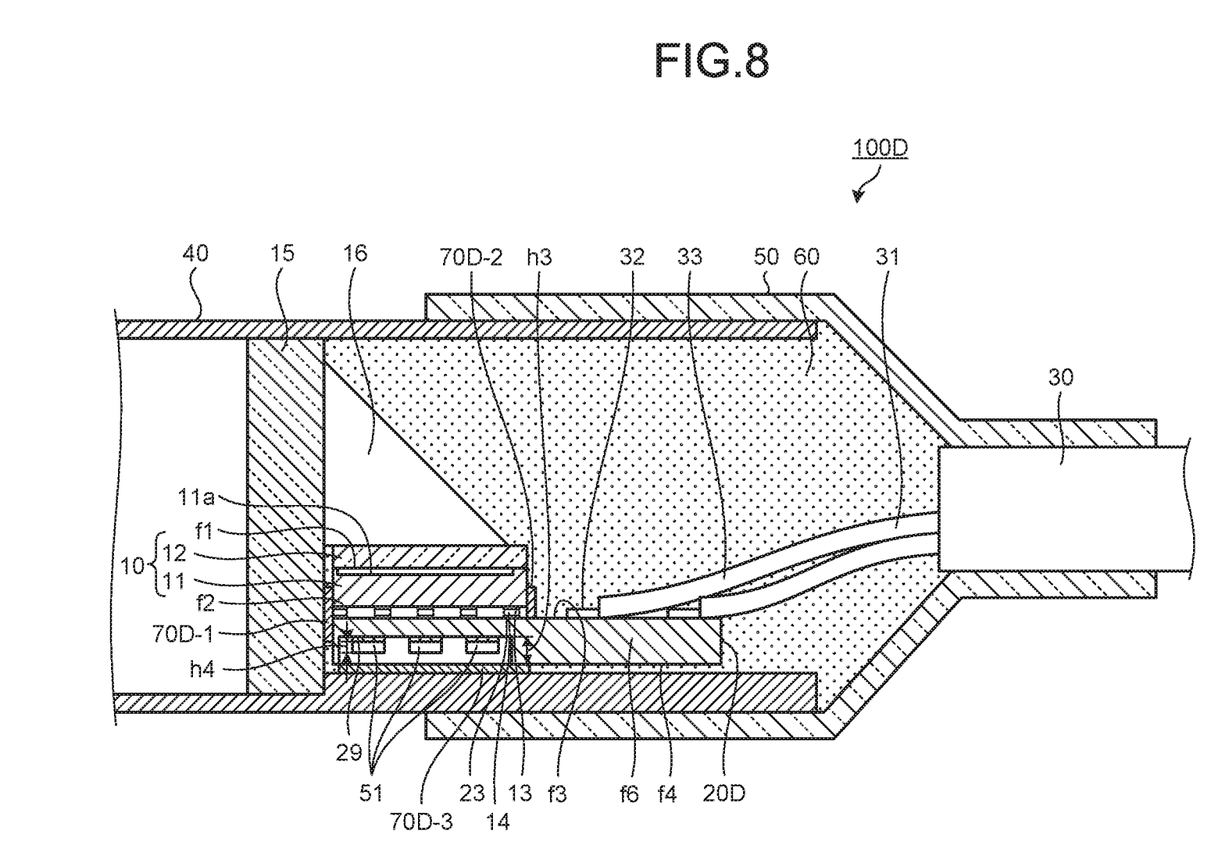
FIG. 8 is a cross-sectional view of an imaging unit according to a third embodiment of the disclosure.
Figure 9:
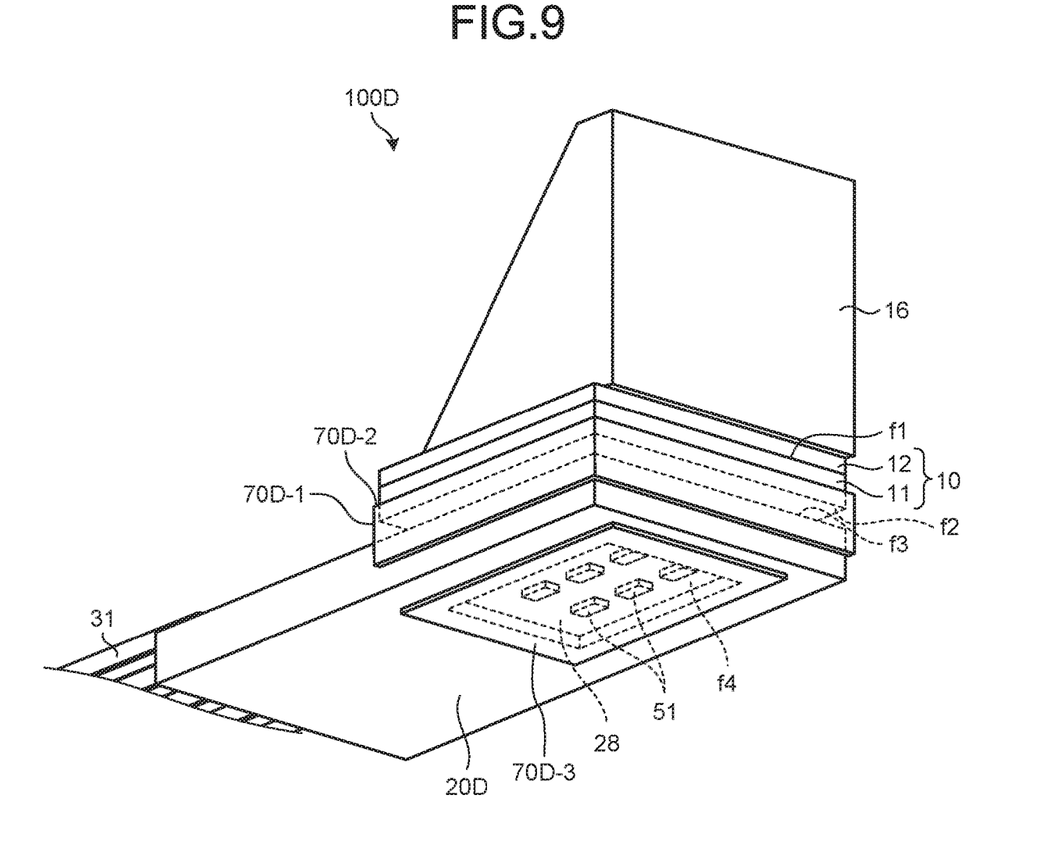
FIG. 9 is a perspective view of the imaging unit illustrated in FIG. 8.
Figure 10:
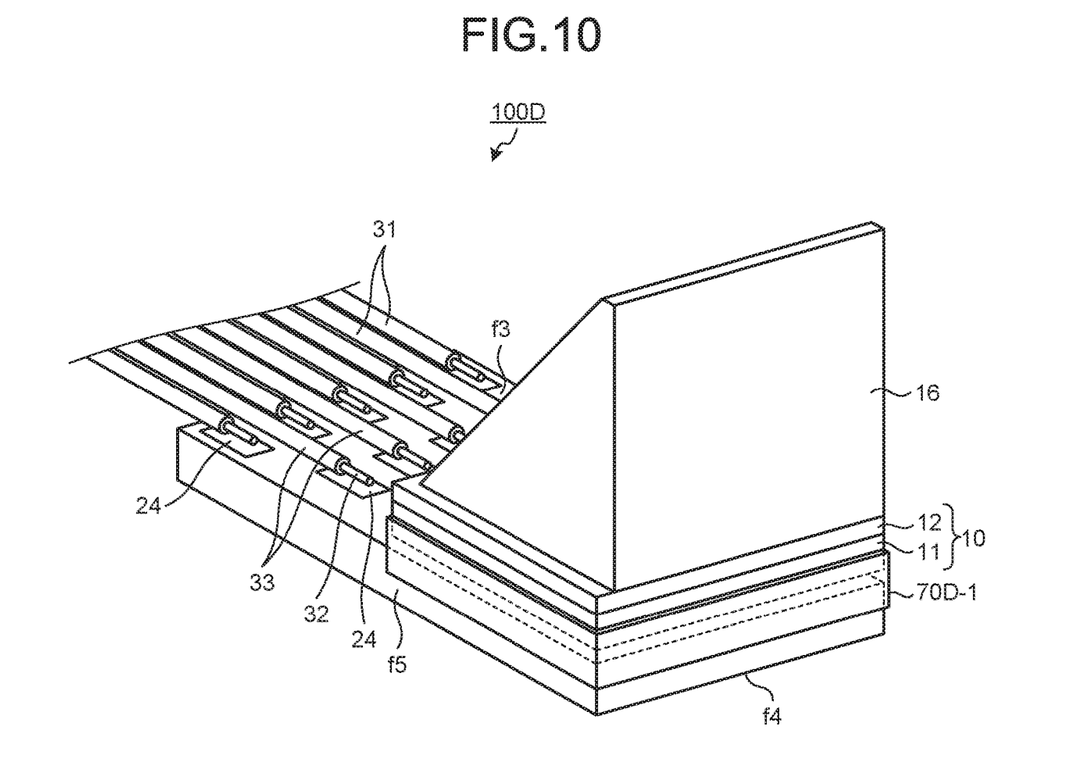
FIG. 10 is a perspective view of the imaging unit illustrated in FIG. 8 when viewed from an upper side.

FIG. 8 is a cross-sectional view of an imaging unit 100D according to a third embodiment of the disclosure. FIG. 9 is a perspective view of the imaging unit 100D illustrated in FIG. 8 and viewed from a lower side. FIG. 10 is a perspective view of the imaging unit 100D illustrated in FIG. 8 when viewed from an upper side. FIG. 9 and FIG. 10 do not illustrate the holder frame 40, the heat shrinkable tube 50, the filler 60, and the centering cover glass 15.

The imaging unit 100D includes a prism 16 that converges and reflects incident light and the imaging device 11 receives the incident light from the prism 16. The semiconductor package 10 is placed with the front surface f1 on which the imaging device 11 is arranged being arranged in parallel with the optical-axis direction, that is, horizontally placed.

On the front surface f3 of a circuit substrate 20D, the connection electrodes 23 that are connected to the sensor electrodes 13 and the cable connection electrodes 24 to which the signal cables 31 are connected are arranged side by side. The concave 28 is formed in the back surface f4 of the circuit substrate 20D. Shortening the circuit substrate 20D in order to shorten the imaging unit 100D narrows the area on which the electronic parts 51 are mounted but forming the concave 28 on the electronic parts 51 are mounted in the back surface of the circuit substrate 20D makes it possible to shorten the imaging unit 100D and thin the imaging unit 100D and further shorten the distance between the electronic parts 51 and the imaging device 11, which enables improvement of electric property.

On the front surface f3 of the circuit substrate 20D, the connection electrodes 23 that are connected to the sensor electrodes 13 and the cable connection electrodes 24 to which the signal cables 31 are connected are arranged side by side in a direction in which the signal cables 31 extend (referred to as the optical-axis direction below). The cable connection electrodes 24 are arranged in a houndstooth pattern (zig-zag) in order to thin the imaging unit 100D while improving the density of the mounted signal cables 31.

In the circuit substrate 20D, the concave 28 is formed in an area of the back surface f4 on which the semiconductor package 10 is mounted and the mount land 29 is arranged on the bottom surface of the concave 28. On the mount land 29, the electronic parts 51 are mounted via conductive members, such as solder.

The concave 28 is formed such that a depth h3 of the concave 28 corresponds to a height that allows, when the electronic parts 51 are mounted on the mount land 29, the top surfaces of the electronic parts 51 not to protrude from the back surface f4 of the circuit substrate 20D, that is, is higher than a height h4 of the electronic parts 51. When the thickness of the circuit substrate 20D is around 0.4 to 0.5 mm, the depth 3 of the concave 28 is preferably around 0.2 to 0.3 mm, that is, approximately half the thickness of the circuit substrate 20D.

The circumference of the joint between the semiconductor package 10 and the circuit substrate 20D and the circumferential area of the concave 28, that is, part of the side surface of the semiconductor package 10 and part of the side surface of the circuit substrate 20D, and the upper part of the concave 28 are covered with cover members 70D-1, 70D-2 and 70D-3 that prevent infiltration of the filler 60. Covering the joint between the semiconductor package 10 and the circuit substrate 20D and the circumferential area of the concave 28 with the cover members 70D-1, 70D-2, and 70D-3 forms an internal space in which air is present around the joints each between the sensor electrode 13 and the first connection electrode 23A and the joints each between the electronic part 51 and the mount land 29.

In the imaging unit 100D according to the third embodiment, covering part of the side surface of the semiconductor package 10, part of the side surface of the circuit substrate 20D, and the circumferential area of the concave 28 with the cover members 70D-1, 70D-2, and 70D-3, respectively, forms the internal space in which air is present around the joints, which makes it possible to reduce the effects on the joints during sterilization processing. Even when a material with large linear expansion is used as the filler 60, it is possible to reduce the effects of humidity on the semiconductor package 10, the circuit substrate 20, and the electronic parts 51 and reduce the effects on the joints during the sterilization processing.

According to the disclosure, covering the joint between a semiconductor package and a circuit substrate with a cover member prevents a filler from infiltrating the joint and keeping air in the internal space covered with the cover member prevents the joint from being destroyed even when the temperature is increased from a normal temperature to a sterilization temperature, which increases reliability of the joint.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging unit comprising:
   a semiconductor package including an imaging device and having a back surface on which a sensor electrode is formed;
   a circuit substrate including a connection electrode that is connected to the sensor electrode via a bump;
   a surrounding part configured to cover the semiconductor package and the circuit substrate;
   a filler with which a space that is enclosed by the surrounding part is filled to seal a circumference of the semiconductor package and the circuit substrate; and
   a first cover configured to prevent the filler from infiltrating a joint between the semiconductor package and the circuit substrate.

2. The imaging unit according to claim 1, wherein the first cover is configured to coat a side surface of the semiconductor package, a side surface of the circuit substrate, and a joint between the side surface of the semiconductor package and the side surface of the circuit substrate together.

3. The imaging unit according to claim 1, wherein
   the circuit substrate includes a first circuit substrate and a second circuit substrate,
   the first circuit substrate has a front surface on which a first connection electrode is formed and has a back surface on which a second connection electrode is formed, the first connection electrode being connected to the sensor electrode of the semiconductor package,
   the second circuit substrate has a front surface on which a third connection electrode is formed and has a side surface on which a cable connection electrode is formed, the third connection electrode being electrically and mechanically connected to the second connection electrode of the first substrate,
   an electronic part is mounted in a concave that is formed in the back surface of the first circuit substrate, and
   the first cover is configured to coat a joint between the semiconductor package and the first circuit substrate and a joint between the first circuit substrate and the second circuit substrate together.

4. The imaging unit according to claim 1, wherein the first cover is a heat shrinkable tube or a resin film.

5. The imaging unit according to claim 1, wherein
an electronic part is mounted in a concave that is formed in a back surface of the circuit substrate and, and
the imaging unit further includes a second cover configured to coat the concave.

6. An endoscope including an insertion unit having a distal end in which the imaging unit according to claim 1 is arranged.

* * * * *